(12) United States Patent
Kuslich et al.

(10) Patent No.: US 6,706,044 B2
(45) Date of Patent: Mar. 16, 2004

(54) STACKED INTERMEDULAR RODS FOR SPINAL FIXATION

(75) Inventors: Stephen D. Kuslich, Stillwater, MN (US); Francis C. Peterson, Prescott, WI (US)

(73) Assignee: Spineology, Inc., Stillwater, MN (US)

( * ) Notice: Subject to any disclaimer, the term of this patent is extended or adjusted under 35 U.S.C. 154(b) by 0 days.

(21) Appl. No.: 10/124,645

(22) Filed: Apr. 17, 2002

(65) Prior Publication Data

US 2002/0169449 A1 Nov. 14, 2002

Related U.S. Application Data

(60) Provisional application No. 60/285,012, filed on Apr. 19, 2001.

(51) Int. Cl.$^7$ .............................................. A61B 17/70
(52) U.S. Cl. ........................................... 606/61; 606/60
(58) Field of Search .................... 606/60, 61, 69, 606/70, 71, 72, 73; 623/17.11

(56) References Cited

U.S. PATENT DOCUMENTS

| | | | |
|---|---|---|---|
| 5,290,289 A | 3/1994 | Sanders et al. ............... | 606/61 |
| 5,324,290 A | 6/1994 | Zdeblick et al. .............. | 606/61 |
| 5,486,174 A | 1/1996 | Fournet-Fayard et al. .... | 606/61 |
| 5,672,175 A * | 9/1997 | Martin ......................... | 606/61 |
| 5,681,311 A | 10/1997 | Foley et al. .................. | 606/61 |
| 5,702,395 A * | 12/1997 | Hopf ............................ | 606/61 |
| 6,056,749 A | 5/2000 | Kuslich ........................ | 606/61 |
| 6,066,140 A | 5/2000 | Gertzbein et al. ........... | 606/61 |
| 6,136,002 A * | 10/2000 | Shih et al. .................... | 606/61 |
| 6,228,085 B1 | 5/2001 | Theken et al. ............... | 606/61 |
| 6,254,603 B1 | 7/2001 | Gertzbein et al. ........... | 606/61 |

FOREIGN PATENT DOCUMENTS

| | | | | |
|---|---|---|---|---|
| FR | 2 702 363 | 3/1993 | | |
| FR | 2 806 615 | 3/2000 | | |
| FR | 2806615 A1 * | 9/2001 | ........... | A61B/17/70 |

* cited by examiner

Primary Examiner—Cary E. O'Connor
Assistant Examiner—Candice C. Melson
(74) Attorney, Agent, or Firm—Vidas, Arrett & Steinkraus, P.A.

(57) ABSTRACT

A spinal fixation system employing bone anchors, several generally parallel rods stacked together and running through each bone anchor, a mechanism for attaching the anchors to the stacked rods and a mechanism for hold the stacked rods together to form a compressed, multi-rod unit.

17 Claims, 5 Drawing Sheets

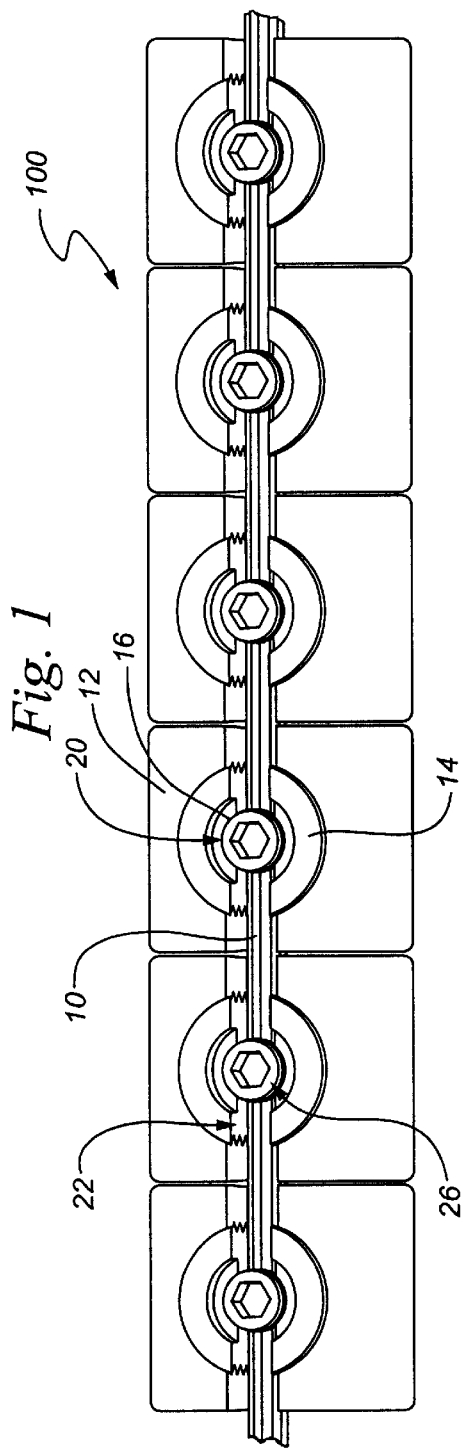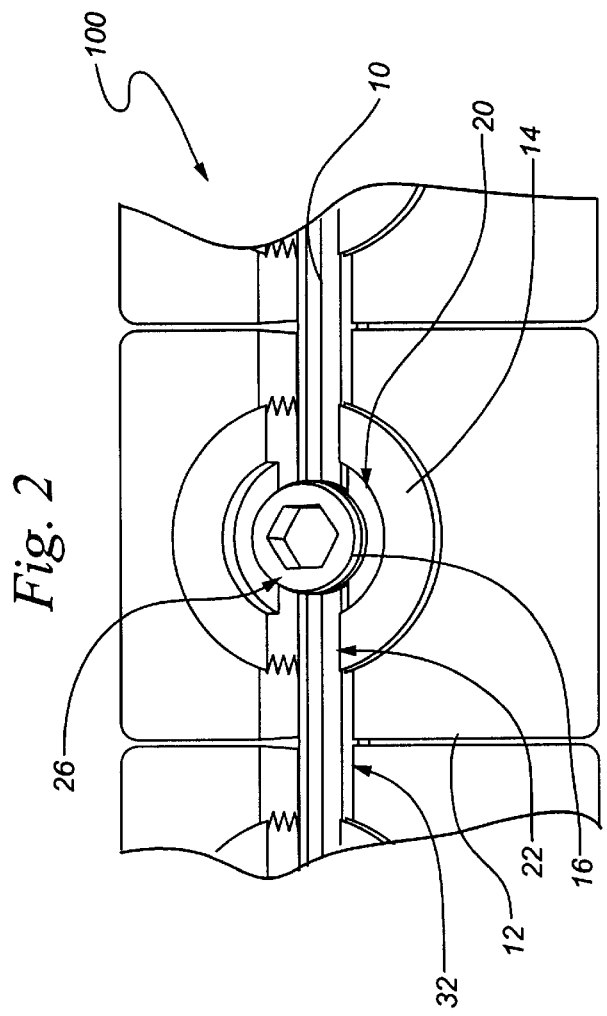

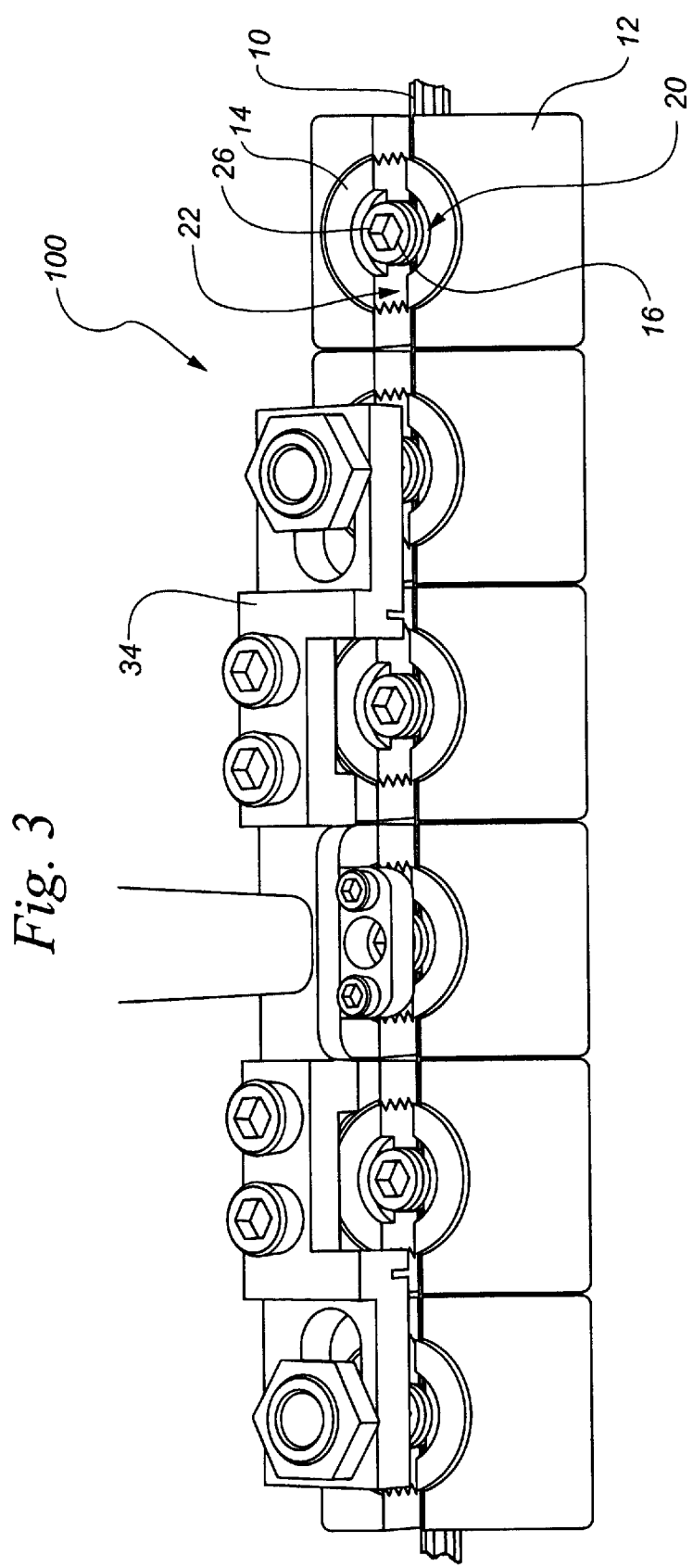

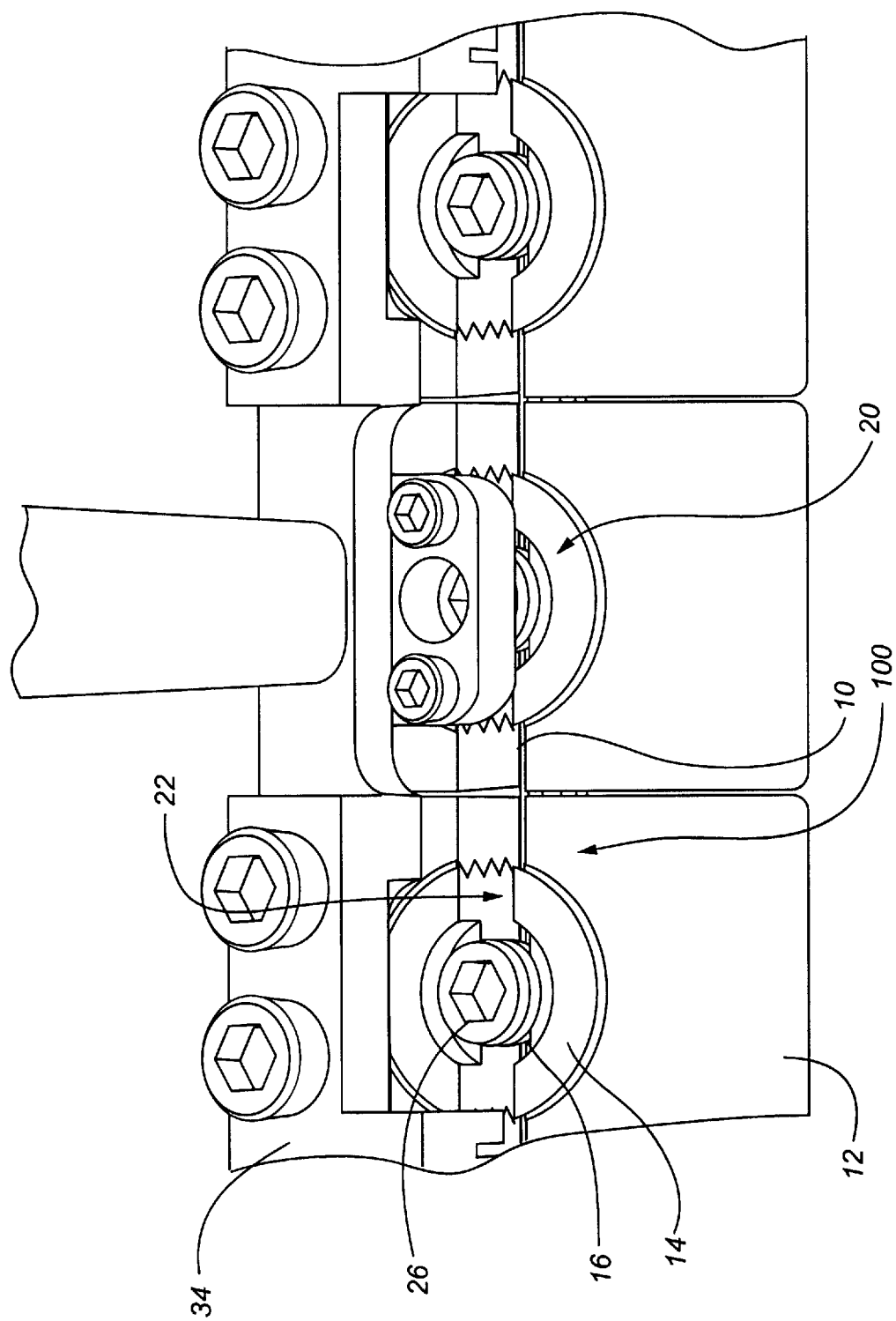

STACKED INTERMEDULAR RODS FOR SPINAL FIXATION

CROSS-REFERENCE TO RELATED APPLICATIONS

This application is a Continuation application from application Ser. No. 60/285,012 filed Apr. 19, 2001 the entire contents of which being incorporated herein by reference.

STATEMENT REGARDING FEDERALLY SPONSORED RESEARCH OR DEVELOPMENT

Not Applicable.

BACKGROUND OF THE INVENTION

Surgical correction of spinal deformity is one of the fundamental achievements of twentieth century Orthopaedics. A number of mechanical techniques have been invented. These include various braces, such as the Milwaukee Brace of Blount and a number of surgical procedures ranging from simple bone grafting (Albee, Hibbs, Moe) to the use of posterior metal hardware systems such as Harrington's rods, and pedicle fixation systems. More recently, experts in the field have developed anterior correction and stabilization systems such as Zielke, Dwyer, Zdeblick and Kanada.

The entire field of spinal deformity is complicated, including the classification of disease and the treatment of the conditions. Numerous classification strategies based on pathology have been suggested, such as infantile, adolescent idiopathic, post-traumatic, neoplastic and neuromuscular.

A classification scheme based on the architectural abnormalities is simpler and more useful to those involved in developing hardware fixation systems. This scheme subdivides the deformities into a small number of sub-types based on the plane of deformity, including:
1. Sagittal plane deformities,
2. Coronal plane deformities, and
3. Rotational deformities.

It must be appreciated that an individual case may possess deformity in more than one plane.

Curved portions of the spine are sometimes differentiated into two types depending on their flexibility and ease of correction with simple changes in posture. These types are:
1) Structural curves, that tend to be stiff—they don't change much with changes in posture, and
2) Compensatory curves, that tend to bend back toward normal by changes in posture.

Structural curves tend to be shorter in length than compensatory curves. Oftentimes, surgeons find that if they can correct the structural curves surgically, the compensatory curves will self-resolve.

For purposes of description, the spine may be divided into two portions; the anterior portion, consisting of the vertebral bodies and the spinal discs; and the posterior portion, consisting of all bony and ligamentous tissue that is posterior to the posterior aspect of the vertebral bodies.

Many, if not most forms of spinal deformity result from pathology in the anterior portion of the spine. Posterior fixation devices are less effective than anterior devices in the correction of anterior pathology. For that reason, many popular fixation devices are designed for anterior placement. Previous attempts to design anterior devices have been troubled with several problems, limitations, and disadvantages. These include:
1. The bulky, exposed metal of anterior devices can irritate and erode delicate visceral tissues such as the aorta, vena cava, the lung and other tissues. In fact, several deaths have resulted from bulky anterior devices used on the anterior surface of the spine. Even newer anterior devices suffer from this limitation; e.g. sturdier, plate-like devices, such as the Yuan device and the Zdeblick Z-Plate should not be applied directly to the anterior aspect of the spine because of the likelihood of aortic erosion (Jendrisak MD. Spontaneous abdominal aortic rupture from erosion by a lumbar spine fixation device: A case report. Surgery 1986;99:631–3).
2. Smaller, thinner anterior devices, such as the Dwyer and Zielke systems are not capable of correcting and holding rotational deformities.
3. Large, stiff rod systems such as the Kostuik-Harrington system or the Kanada device and similar systems are difficult to custom fit to the desired degree of bending because the large stiff rods must be permanently deformed before final placement into the body. It is very difficult, if not impossible, to deform the rod to the desired bend without permanently damaging the metal structure of the device.

While the present invention is useful for posterior application, it is expected that its use would be most commonly performed from the anterior direction. The current invention teaches a novel device that allows the surgeon to correct and stabilize many types of deformities via the anterior column of the spine. The device solves most of the problems listed above. If the stacked rods of this invention were substituted for the single non-round rod of the Spineology K-Centrum® System (U.S. Pat. No. 5,591,235) the resulting system would have the advantages of containment within the external margin of the spinal bones—and therefore the safety afforded by the lack of protrusions into delicate visceral structures—and the advantages of conformability and ease of use to be described in the following device description.

For many of the reasons outlined below, it is expected that the device will be more versatile, more stable and safer to use than other forms of correction and stabilization.

Rather than a large rigid single rod, e.g. the Harrington-Kostuik device, or double large rigid rods intentionally separated by a plate, e.g., the Kanada device, or a large rigid plate, e.g., the Z-Plate, this invention utilizes several small diameter, flexible rods. When these rods are stacked closely together and compressed against each other by a tightening means, such as a screw or clamp, the group of rods develops the rigidity of the single larger rods or plates, and therefore can support spinal loads far greater than they would otherwise be capable of. The advantage offered by this invention is the ability to place the flexible rods into position without permanently deforming their structure, i.e. by not deforming them beyond the yield point defined by Young's modulus for the material, as would be necessary in more bulky rigid devices.

This allows the surgeon to place the rods with finger forces only, without damaging the structure of the rod. In a later stage of the operation, the surgeon is able to manipulate the stacked rods into the appropriate position and tighten a tightening device associated with the rods, thereby creating a rigid construct, but without the necessity of removing the rods from the construct, bending them on the back table, and then replacing the rod into position in the construct. This capability should reduce operative time, reduce blood loss, and avoid damage and permanent deformity of the rods—and consequent damage to their metallic structure. For these and other reasons, the present device is theoretically easier, faster, safer and more secure than competitive devices.

The art described in this section is not intended to constitute an admission that any patent, publication or other information referred to herein is "prior art" with respect to this invention, unless specifically designated as such. In addition, this section should not be construed to mean that a search has been made or that no other pertinent information as defined in 37 C.F.R. §1.56(a) exists.

BRIEF SUMMARY OF THE INVENTION

The invented device comprises four basic components: a bone anchor component, a plurality of rods, a means for attaching the anchors to the rods, and a means for compression or clamping the rods together.

The bone anchors ensure that the present device is properly secured to the spinal bones. The bone anchors may be slotted screws, staples, bolts, hooks or clamps. In a preferred embodiment, the bone anchors may be large hollow slotted vertebral body anchors such as the K-Centrum® bone anchors.

The rods comprise at least two moderately flexible rods which run essentially parallel together in a stacked fashion. The rods may be comprised of a variety of materials including: steel, titanium, Nitinol, a composite material such as carbon fibers mixed with a resin or cement, or any other sufficiently strong biocompatible material. In order to fit the human spine, they may be about 0.5 to 3 mm in diameter and their lengths may be sized to fit the length of the curve to be corrected.

The means of attaching the anchors to the stacked rods may be embodied in a variety of features which may be inherent in the anchor and/or rod construction. For example the anchors may include one or more slots for receiving the rods. Similarly, the rods and/or anchors may include one ore more grooves, projecting loops, or other feature for mutual engagement. Additionally or alternatively, a separate attachment device may be used to attach the rods and anchors such as one or more staples or clamps.

The means of clamping or otherwise compressing the rods together to form a compressed, multi-rod single unit may be embodied in a variety of elements such as a setscrew in a slot, a gripping jaw, or a circumferential tension band, among others.

The advantages of this novel system will be immediately apparent to those skilled in the art.
1. The system allows the individual rods to be placed in the uncorrected spine without permanent deformation of the metal.
2. The spinal deformity can be slowly corrected. Slow correction of the deformity is less traumatic and less likely to damage delicate nerve tissue and blood supply to the spinal cord.
3. It is at least theoretically possible to perform the invented procedure using minimally invasive techniques such as laparoscopic or thoracoscopic techniques because the rods can be bent during insertion, allowing positioning of the hardware around delicate internal structures.
4. The system is highly adjustable in terms of rotational and bending directions, so the surgeon can make fine adjustments without the necessity of removing the rods and force bending the rods outside of the body, as is the case in almost all competitive system. This feature will decrease the time of operation and safety factor by reducing the likelihood of over-correction or under-correction.
5. The system, in the preferred embodiment, using deeply set slotted anchors, when fully installed, is entirely contained within the outer spinal margins. No part of the device is outside of the spine where metal parts are prone to irritate and erode visceral structures such as the aorta, vena cava, or lung or other organ tissues.
6. Unlike a single rod system, a stacked rod system is less prone to catastrophic failure, i.e., a stress riser leading to failure of a single rod does not immediately propagate to the other rods. In other words, one rod can fail without collapse of the entire construct.

BRIEF DESCRIPTION OF THE DRAWINGS

A detailed description of the invention is hereafter described with specific reference being made to the drawings in which:

FIG. 1 is a top view of an embodiment of the invention as seen implanted into a plurality of vertebral bodies;

FIG. 2 is a close up view of a portion of the embodiment shown in FIG. 1;

FIG. 3 is a side elevational view showing the stacked rods and bone anchors secured to multiple vertebral bodies with an aligning tool in place;

FIG. 4 is an enlarged top view showing bone anchors with stacked rods secured to multiple vertebral bodies with an aligning tool in place;

DETAILED DESCRIPTION OF THE INVENTION

Figure 5:
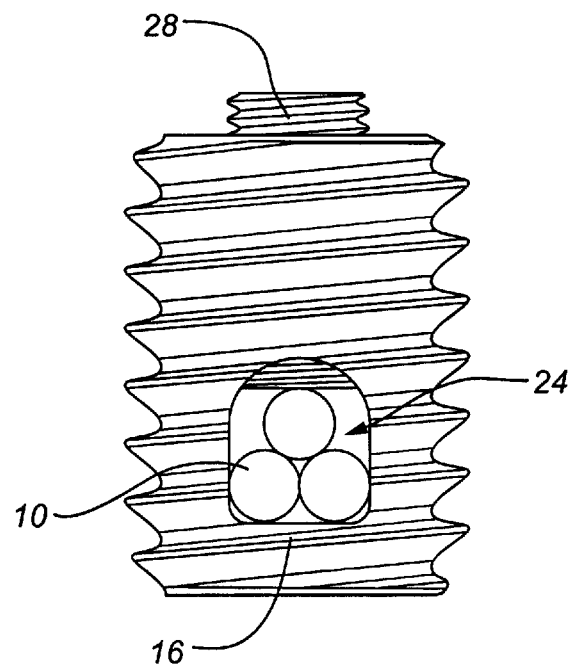
FIG. 5 is a side view of a bone anchor showing the stacked rods as they pass therethrough.

Correction of spinal deformity involves several sequential or simultaneous actions to reposition the spatial orientation of vertebral elements. In order to accomplish such repositioning, the surgeon must accomplish the following tasks:
1. Gain exposure of the anatomy
2. Release bony or soft tissue tethering tissues (to allow correction to happen)
3. Gain a purchase on the vertebral element (to apply mechanical forces during correction maneuvers
4. Apply the correcting forces (shortening, lengthening, bending, or rotation)
5. Lock the fixation system to hold the correction.

In reference to the various figures included herein, a preferred embodiment of the inventive system is shown generally at reference numeral 100. As may be seen in FIGS. 1–4 the inventive device 100 includes a plurality of rods 10 which are positioned within each of the vertebral bodies 12 by an anchor 14 and a rod securement member 16. The anchor 14 is surgically inserted into each vertebral body 12.

The anchors 14 each include a housing 20 which defines a longitudinal slot 22. The housing 20 may be threaded to permit a rod securement member 16 to be threadingly engaged therein. As may best be seen in FIG. 5, each of the rod securement members 16 defines a horizontal passage or chamber 24, through which the rods 10 are inserted and retained. As may be seen in FIGS. 1–4, when each of the rod securement members 16 are inserted into the respective housing 22 of each anchor 14, each horizontal chamber 24 is oriented in a direction corresponding to the longitudinal orientation of the slot 22. As may be seen in FIGS. 6 and 7, the continuous longitudinal orientation of the horizontal chambers 24 ensures that the rods 10 may be freely inserted within the rod securement members 16 and extend therethrough.

As may be seen in FIGS. 1–4, the rod securement members 16 also define a second or vertical passage or chamber 26. The vertical chamber 26 may be threaded for threadingly receipt of a locking screw. As may best be seen in FIG. 2, the vertical chamber 26 intersects the horizontal chamber 24. As a result, when the rods 10 are positioned within the horizontal chamber, a locking screw 28, such as may be seen in FIG. 5, may be threadingly inserted into the vertical chamber 26 and advanced such that the screw 28 contacts one or more of the rods 10. By tightening the screw 28 into the vertical chamber 26 and against the rods 10, the screw 28 produces sufficient friction to stop relative motion between the rods 10, thus producing a "composite rod" that behaves as a single solid rod once the screw 24 is tightened and the rods 10 are compressed together, such as is depicted in FIGS. 5–7.

Figure 6:
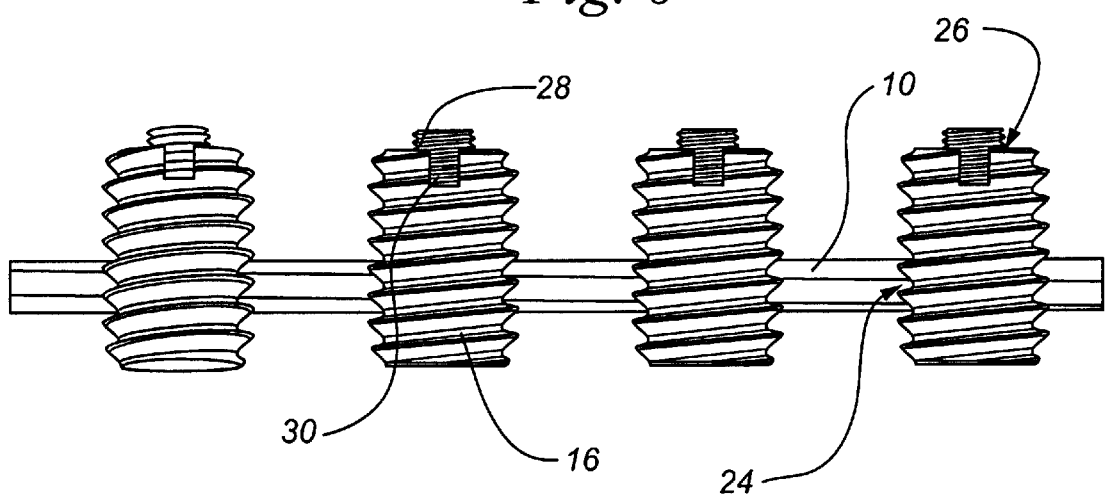
FIG. 6 is a side view of an embodiment of the invention wherein securement members are shown disposed about the rods and displaced at varying angles relative to one another.
Figure 7:
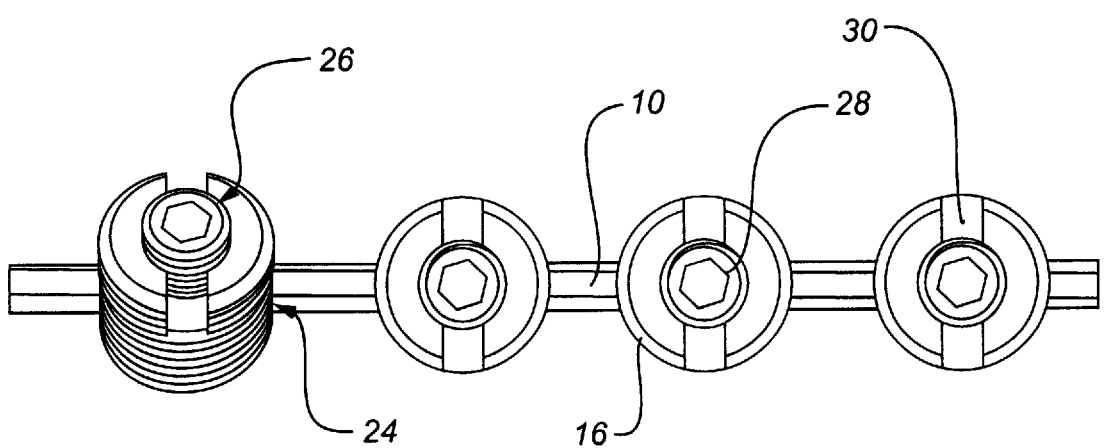
FIG. 7 is a top view of the embodiment shown in FIG. 6

In FIGS. 6 and 7 a plurality of securement members 16 are shown outside of the vertebral bodies and without anchors. As may be seen, the rods 10 are secured within each of the securement members with respective screws 28.

The present invention 100 may be constructed in a wide variety of embodiments and include a plethora of different components other than the precise examples described herein. However, in the various embodiments shown herein the anchors 14 may be comprised of a large, partly hollow, threaded, cylindrical slotted vertebral anchor, such as or similar to, the K-Centrum® System anchors described in U.S. Pat. No. 5,591,235, the entire contents of which being incorporated herein by reference.

Various means may also be used to manipulate the various elements of the invention described herein. For example, as may be seen in FIGS. 6 and 7, the rod securement members 16 may include surface features such as an engagement slot 30 to which a tool such as a screw driver may be engaged to thread the member 16 into the anchor 14 as previously described. The anchors themselves as well as the screws may likewise be equipped with additional features to aid in their respective manipulation.

Insertion of the inventive system 100 may be conducted as follows:

In the case of anterior exposures, the surgeon makes an incision and then moves non-spinal tissues aside. He then performs whatever soft tissue releases are necessary. At that point, the surgeon would insert bone anchors 14 into the involved vertebral bodies 12 and the securement members 16, at the appropriate entrance points and to the appropriate depth, and at the appropriate angle.

Next, the surgeon installs several moderately flexible rods 10 to form the stacked rod composite 32, such as may best be seen in FIG. 2, into the horizontal chambers provided in the securement members 16. Then, locking screws 28 are loosely placed to hold the rods in place, but not so rigidly held as to prevent movement between the rods and the anchors. Then, the surgeon uses appropriate maneuvers and or tools 34, such as are depicted in FIGS. 3 and 4 to manipulate the spine into the desired position. For example, he might apply forces to the appropriate anchors 14 to adjust the spatial position of the anchors, and therefore the vertebral bodies, to the corrected position and orientation. Finally, the surgeon fully tightens the locking screws 28 into position, thus producing a great deal of friction between the rods 10, and thereby forcing the stacked rods to function as if they were a single large rod.

While this invention may be embodied in many different forms, there are shown in the drawings and described in detail herein specific preferred embodiments of the invention. The present disclosure is an exemplification of the principles of the invention and is not intended to limit the invention to the particular embodiments illustrated.

This completes the description of the preferred and alternate embodiments of the invention. Those skilled in the art may recognize other equivalents to the specific embodiment described herein which equivalents are intended to be encompassed by the claims attached hereto.

What is claimed is:

1. A device for correction and stabilization of spinal deformity consisting of:

(a) at least two bone anchors for attaching the device to the spine, (b) at least two stacked rods running generally parallel to one another, the stacked rods have a longitudinal shape and length, and a cross sectional shape and cross sectional diameter, the at least two stacked rods being immediately adjacent one another along their length;

(c) means for connecting the rods to the bone anchors, wherein the rods are in direct contact with the bone anchors when connected thereto;

(d) means for compressing the rods tightly together.

2. The device of claim 1 wherein the bone anchors, at least partly, consist of threaded screws or threaded cylinders or bolts.

3. The device of claim 1 wherein the bone anchors, at least partly, consists of clamps or hooks.

4. The device of claim 1 wherein the stacked rods are constructed of a biocompatible metal or a biocompatible polymeric material, or a composite of various biocompatible materials.

5. The device of claim 1 wherein the stacked rods are constructed of a memory metal.

6. The device of claim 1 wherein cross sectional shape of the stacked rods is circular or elliptical.

7. The device of claim 1 wherein the stacked rods are knurled on their surfaces.

8. The device of claim 1 wherein the cross sectional diameters of the stacked rods are identical.

9. The device of claim 1 wherein the cross sectional diameters of the stacked rods are dissimilar.

10. The device of claim 1 wherein the means for connecting the rods to the bone anchors is a slot in the bone anchor and a compression screw, which when turned into a threaded channel in the bone anchor, forces (biases) the rods against the floor of the slot.

11. The device of claim 1 wherein the means for connecting the rods to the bone anchors is a clamp.

12. The device of claim 1 wherein the means for connecting the rods to the bone anchors is a compression ring.

13. The device of claim 1 wherein the means for compressing the rods tightly together is a slot in the bone anchor and a compression screw, which when turned into a threaded channel in the bone anchor, forces (biases) the rods against the floor of the slot.

14. The device of claim 1 wherein the means for compressing the rods tightly together is a clamp.

15. The device of claim 1 wherein the means for compressing the rods tightly together is a compression ring.

16. The method of spinal deformity correction, utilizing any of the devices of claim 1, consisting of the following maneuvers:

exposing the spinal bones to be stabilized or corrected;

releasing the tethering tissues, if necessary for deformity correction;

removing or debriding the spinal disc joints, if necessary;

placing the at least two bone anchors into the vertebral bodies, or the pedicles of the spinal bones, or the lamina of spinal bones, or the spinous processes on the spinal bones or any other purchase area of the spinal bones, or the region of the spine to be instrumented;

placing the at least two stacked rods, into the means of attachment to the bone anchors;

correcting the misalignment or other structural deformity, if necessary;

compressing or biasing the rods tightly together using the means of attachment to the bone anchors and/or other means;

preparing the appropriate surface of the spinal bone to accept bone or other grafting materials, if necessary;

applying bone graft or other materials designed to encourage bone growth, if necessary; and closing the exposed tissues by suture or other means, if necessary.

17. The method of claim 16, wherein the at least two stacked rods comprise two or more sets of the at least two stacked rods and their accompanying means of attachment and means of compression.

* * * * *